(12) United States Patent
Hess et al.

(10) Patent No.: US 7,927,812 B2
(45) Date of Patent: Apr. 19, 2011

(54) CARDIAC TROPONIN AS AN INDICATOR OF CORONARY ARTERY DISEASE

(75) Inventors: Georg Hess, Mainz (DE); Andrea Hess, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 37 days.

(21) Appl. No.: 11/837,714

(22) Filed: Aug. 13, 2007

(65) Prior Publication Data

US 2008/0081344 A1 Apr. 3, 2008

(30) Foreign Application Priority Data

Aug. 16, 2006 (EP) ..................................... 06119017

(51) Int. Cl.
*G01N 33/48* (2006.01)
*G01N 33/50* (2006.01)
(52) U.S. Cl. ........................ 435/7.1; 435/7.21; 435/7.8
(58) Field of Classification Search .................. None
See application file for complete search history.

(56) References Cited

U.S. PATENT DOCUMENTS

| 5,744,305 A | 4/1998 | Fodor et al. |
| 2006/0234304 A1 | 10/2006 | Amann-Zalan et al. |

FOREIGN PATENT DOCUMENTS

| CA | 2428460 A1 | 11/2003 |
| EP | 0648228 B1 | 4/1995 |
| EP | 1363128 A2 | 11/2003 |
| WO | 02/083913 A1 | 10/2002 |
| WO | 02/089657 A2 | 11/2002 |
| WO | 2004/103150 A2 | 12/2004 |
| WO | 2005/043169 A1 | 5/2005 |

OTHER PUBLICATIONS

Al-Mallah,M. et al., "Positive Troponin in Diabetic Ketoacidosis without Acute Coronary Syndrome Predicts Poor Outcome," Circulation, 110,17. Suppl. S (Oct. 2004) 413.
Anderson, P. et al., "Molecular Basis of Human Cardiac Troponin T Isoforms Expressed in the Developing, Adult, and Falling Heart," Circulation Research, 76:4 (Apr. 1995) 681-686.
Bonow, R. et al., "New Insights into the Cardiac Natriuretic Peptides," Circulation, 93 (1996) 1946-1950.
DeFilippi, C. et al., "Cardiac Troponin I and C-Reactive Protein for Predicting Prognosis, Coronary Atroscierosis, and Cardiomyopathy in Patients Undergoing Long-Term Hemodialysis," JAMA, 290;3 (Jul. 16, 2003) 353-359.
Ferrieres, G. et al., "Human Cardiac Troponin I: Precise Identification of Antigenic Epitopes and Prediction of Secondary Structure," Clinical Chemistry, 44;3 (1998) 487-493.
Hojs, R. et al., "Cardiac Troponin (T) in Hemodialysis Patients with Asymptomatic and Symptomatic Atherosclerosis," Archives of Medical Research 36 (2005) 367-371.
Karl, J. et al., "Development of a Novel, N-Terminal- proBNP (NT-proBNP) Assay with a Low Detection Limit," Scand J Clin Lab Invest, 59(suppl 230) (1999) 177-181.
Mueller, T. et al., "Long-term stability of endogenous B-type natriuretic peptide (BP) and amino terminal proBNP (NT-proBNP) in frozen plasma samples," Clin Chem Lab MED, 42;8 (2004) 942-944.
Nolan, J. et al., "Suspension array technology: evolution of the flat-array paradigm," Trends in Biotechnology, 20, 1 (Jan. 2002) 9-12.
Smith, M, et al., "Delayed Metabolism of Human Brain Natriuretic Peptide Reflects Resistance to Neutral Endopeptidase," Journal of Endocrinology, 167 (2000) 239-246.Clinical Chemistry, 50:5 (2004) 867-873.
Wu, A. et al., "Analytical and Clinical Evaluation of the Bayer ADVIA Centaur Automated B-Type Natriuretic Peptide Assay in Patients with Heart Failure A Multisite Study," Clinical Chemistry, 50:5 (2004) 867-873.
Yeo, K, et al., "Multicenter Evaluation of the Roche NT-proBNP Assay and Comparison to the Biosite Triage BNP Assay," Clinica Chimica Acta, 338 (2003) 107-115.
Zethelius, B. et al., "Troponin I as a Predictor of Coronary Heart Disease and Mortality in 70-Year-Old Men," Circulation 113:8 (Feb. 28, 2006) 1071-1078.
"Myocardial Infarction Redefined-A Consensus Document of the Joint European Society of Cardiology/American College of Cardology Committee for the Redefinition of Myocardial Infarction," Journal of the American College of Cardiology, 36;3 (2000) 959-969.

*Primary Examiner* — Elizabeth C. Kemmerer

(57) ABSTRACT

The present invention relates to a method for diagnosing an advanced ischemic coronary heart disease comprising the steps of determining an amount of a cardiac troponin in a sample of a subject and diagnosing the disease by comparing the amount determined with a reference amount of the cardiac troponin.

2 Claims, No Drawings

CARDIAC TROPONIN AS AN INDICATOR OF CORONARY ARTERY DISEASE

RELATED APPLICATIONS

This application claims priority to European application EP 06119017.9 filed Aug. 16, 2006.

FIELD OF THE INVENTION

The present invention relates to a method for diagnosing in a subject the pathological state of an advanced ischemic coronary heart disease which is preferably related to a coronary vessel disease, in particular a multi-vessel disease. The method comprises the steps of determining the amount of a cardiac troponin in a sample of a subject and diagnosing said coronary heart disease, preferably the coronary vessel disease, in particular the multi-vessel disease by comparing the amount determined with reference amounts. Also comprised by the present invention are devices and kits for carrying out such methods.

BACKGROUND OF THE INVENTION

An aim of modern medicine is to provide personalized or individualized treatment regimens. Those are treatment regimens which take into account a patient's individual needs or risks. A particularly important risk is the presence of a cardiovascular complication, particularly an unrecognized cardiovascular complication, or a predilection for such cardiovascular complications. Cardiovascular complications, particularly heart diseases, are the leading cause of morbidity and mortality in the Western hemisphere. Cardiovascular complications can remain asymptomatic for long periods of time. Therefore, reliable differential diagnosis of the presence of a cardiovascular complication is more difficult and error-prone than generally believed.

Specifically, patients suffering from symptoms of an acute cardiovascular event (e.g., myocardial infarction or MI) such as chest pain are currently subjected to a troponin T based diagnosis. To this end, troponin T levels of the patients are determined. If the amount of troponin T in the blood is elevated, i.e. above 0.1 ng/ml, an acute cardiovascular event is assumed and the patent is treated accordingly.

MI is classified as belonging to coronary heart diseases (CHD) and is preceded by other events also classified as belonging to CHD, like unstable angina pectoris (UAP). Symptomatic for UAP is chest pain which is relieved by sublingual administration of nitroglycerin. UAP is caused by a partial occlusion of the coronary vessels leading to hypoxemia and myocardial ischemia. In case the occlusion is too severe or total, a myocardial necrosis (which is the pathological state underlying myocardial infarction) results. MI may occur without obvious symptoms, i.e. the subject does not show any discomfort, and the MI is not preceded by stable or unstable angina pectoris.

UAP, however, is a symptomatic event preceding MI. A CHD in a subject may also occur symptomless, i.e. the subject may not feel uncomfortable or exhibit any signs of CHD like shortness of breath, chest pain or others known to the person skilled in the art. The subject, however, may be pathological and suffer from a malfunction of his coronary vessels which may result in an MI and/or congestive heart failure CHF, meaning the heart does not have the capacity to perform as required in order to ensure the necessary provision of blood to the subject's body. This may result in severe complications, one example of which is cardiac death.

It is known that subjects belonging to risk groups (e.g. smokers and diabetes patients) are more prone to suffering from CHD or CHF than subjects not exposed to risk factors (healthy subjects). Often, the asymptomatic forms of CHD/CHF occur, resulting in the pathological state remaining unrecognized. Hints for the occurrence of CHD are taken from the Framingham score or the PROCAM score. To date, the physiological conditions of the coronary vessels are generally evaluated by coronary angiography (invasive or virtual) being expensive and requiring elaborate and time-consuming procedures. Subjects which are not highly suspicious of suffering from a coronary vessel complication will in general not be subjected to coronary angiography.

SUMMARY OF THE INVENTION

The object of the present invention is to provide a new test to determine an advanced ischemic coronary heart disease, preferably related to a coronary vessel disease, in particular a multi-vessel disease. The test should be easy to be carried out, not require costly equipment/apparatuses and, preferably, not the knowledge of a specialist in the field of cardiovascular diseases.

The present invention solves this problem by a method for diagnosing an advanced ischemic coronary heart disease comprising the steps of determining the amount of a cardiac troponin in a sample of a subject and diagnosing the disease by comparing the amount determined with reference amounts.

Preferably, the coronary heart disease is related to a coronary vessel disease, particularly to a multi-vessel disease. In particular, the advanced ischemic coronary heart disease is symptomless.

The method of the present invention, preferably, is an in vitro method. Moreover, it may comprise steps in addition to those explicitly mentioned above. For example, further steps may relate to sample pre-treatments or evaluation of the diagnostic data.

DETAILED DESCRIPTION OF THE INVENTION

The term "diagnosing" as used herein refers to assessing the probability according to which a subject is suffering from an advanced ischemic coronary heart disease or any other disease referred to in this specification. As will be understood by those skilled in the art, such an assessment is usually not intended to be correct for 100% of the subjects to be diagnosed. The term, however, requires that a statistically significant portion of subjects can be diagnosed (e.g. a cohort in a cohort study) to suffer from heart failure or to have a risk of suffering from the disease in the future. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

Diagnosing according to the present invention includes monitoring, confirmation, subclassification and prediction of the relevant disease, symptoms or risks therefor. Monitoring relates to keeping track of an already diagnosed disease, or complication, e.g. to analyze the progression of the disease or the influence of a particular treatment on the progression of disease or complication. Confirmation relates to the strengthening or substantiating a diagnosis already performed using other indicators or markers. Subclassification relates to further defining a diagnosis according to different subclasses of the diagnosed disease, e.g. defining according to mild or severe forms of the disease. In the present case, this is related to distinguishing a single vessel from a multi-vessel disease. Prediction relates to prognosing a disease or complication before other symptoms or markers have become evident or have become significantly altered. In particular, the present invention relates to monitoring, confirmation, and subclassification.

As mentioned above, CHD may occur symptomless, or the subject concerned may show symptoms. The present invention lends itself for the determination of symptomless subjects having CHD. The subject in general belongs to risk groups like smokers, diabetic patients, obese patients, subjects suffering from hyperlipemia, subjects suffering from arterial hypertension, subjects with a family history of coronary heart disease, myocardial infarction or stroke, persons with a base disease associated with an elevated frequence of a coronary heart disease like, for example, rheumathoid arthritis.

Preferably, the subject suffers from CHD caused by a coronary vessel disease. In particular, the vessel disease is a multi-vessel disease, i.e. caused by a partial occlusion of a heart vessel, e.g. by plaque deposit, thrombi and/or spasms. A partial vessel occlusion results in a myocardial ischemia which may give rise to further complications occurring with or without symptoms. Coronary vessels are known to the person skilled in the art. In the context of the present invention, the term "coronary vessels" comprises the (three) large coronary vessels as well as the medium size vessels and the small size vessels connected thereto. Thus, in the context of the present invention, the coronary vessel disease may, for example, occur as a macroangiopathy affecting the large coronary vessels, but also as a combined macro- and microangiopathy.

In case a total occlusion of a heart vessel occurs, the resulting pathological state is a myocardial necrosis which is defined as being the state underlying myocardial infarction MI. It is state of the art to diagnose a MI by measuring the amount of cardiac troponin T (TnT) or troponin I (TnI) in a body liquid of the subject. If the value is raised, a MI is suspected to have occurred. The method of diagnosing MI (which is a coronary heart disease as such) is not a part of the present invention.

In the context of the present invention, the term "coronary heart disease" CHD means any coronary dysfunction (pathological state) resulting from coronary arteriosclerosis, i.e. partial or total occlusion of coronary vessels. The term CHD includes a wide range of various acute and chronic pathological states comprising stable and unstable angina pectoris (SAP and UAP, respectively), left ventricular dysfunction LVD, (congestive) heart failure (CHF), myocardial death. More general, in the context of the present invention, the term relates to lack of blood supply to the myocardium and to every pathological state entrained thereby.

In general, SAP, UAP, and MI are regarded as being an acute pathological state or disease whereas LVD and CHF are regarded as being chronic states or diseases. The present invention is in particular appropriate for determining a CHD which is symptomless. Thus, SAP and UAP, which are not symptomless, will in general not be diagnosed using the teachings of the present invention for showing characteristic symptoms like chest pain. The diagnosis of MI is likewise not an object of the present invention. The present invention pertains to chronic heart vessel diseases leading to pathological states like, for example, LVD and/or CHF.

In the context of the present invention "symptomless" means that the subject does not show any obvious symptoms for CHD. "Obvious symptoms" are those symptoms which the person skilled in the art (a physician) will recognize as being characteristic for the respective pathological state, which here is CHD or a subgroup within CHD. A symptomless patient does, in the context of the present invention, not show a limitation of physical activity, ordinary physical activity does not cause undue fatigue, palpitation dyspnea (shortness of breath), nausea, vomiting, or anxiety. Of course, the subject does not show severe symptoms like chest pain.

It is clear to the person skilled in the art that the term "obvious symptoms" does not include symptoms which are found after intensive and/or targeted medical examination like e.g. angiography or ECC. It has to be borne in mind that every pathological state entrains symptoms which can in general be recognized if the medical examination is carried out with sufficient care (in an intensive way).

A coronary heart disease CHD may result in an acute cardiovascular event, i.e. an event which suddenly appears, i.e. without previous clinical signs or symptoms, and which severely affect the diastolic or systolic blood flow rate. Histopathologically, the acute cardiovascular event referred to herein shall be caused by a sudden ischemia of heart muscle cells accompanied by severe necrosis of said cells. Generally, the subject suffering from an acute cardiovascular event will also suffer from typical symptoms such as chest, epigastric, arm, wrist or jaw discomfort or pain whereby the chest pain may radiate to the arm, back or shoulder. Further symptoms of an acute cardiovascular event may be unexplained nausea or vomiting, persistent shortness of breath, weakness, dizziness, lightheadedness or syncope as well as any combinations thereof. Generally, an acute cardiovascular event is referred to as an acute coronary syndrome (ACS), i.e. either an unstable angina pectoris (UAP) or myocardial infarction (MI). In many cases, the acute cardiovascular event is MI including ST-elevated MI and non-ST-elevated MI. Moreover, the cardiovascular event also encompasses stroke. Further details on the definitions, symptoms and clinical signs such as electrocardiographic signs, are found in Joint European Society of Cardiology/American Society of Cardiology, 2000, J American College of Cardiology, Vol. 36, No. 3: 959-969.

In the context of the present invention, a coronary heart disease will in general, with or without previously passing the stage of an acute cardiovascular event or the state of LVD, result in heart failure which is classified into several classes. Symptoms may be classified according to the New York Heart Association classification system. Patients of Class I have no obvious symptoms of cardiovascular disease. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased. Accordingly, patients can be divided into subjects showing no clinical symptoms and those with symptoms (e.g. dyspnea).

In a preferred embodiment of the present invention, the amount of a natriuretic peptide selected from the group consisting of ANP, NT-proANP, BNP and NT-proBNP, preferably BNP or NT-proBNP, in particular NT-proBNP, or a variant of the named peptides, is measured, in addition to the cardiac troponin, in particular, TnT.

The natriuretic peptides, in particular NT-proBNP, are known as so-called neurohumoral markers indicating wall stress on the myocardium which can be related to e.g. heart failure, myocardial ischemia and or myocardial necrosis.

In the context of the present invention, the determination of the amount of a natriuretic peptide or a derivative thereof, in particular NT-proBNP, permits to obtain additional information on the degree of the ischemic coronary heart disease, in particular if a multi-vessel disease of the respective subject is at hand.

The term "subject" as used herein relates to animals, preferably mammals, and, more preferably, humans. However, it is envisaged by the present invention that the subject shall preferably not exhibit symptoms known to be associated with CHD or with an acute cardiovascular event, i.e. chest pain, dyspnea and others as described above. More preferably, the subject shall not exhibit symptoms according to NYHA classes II, III or IV. In one embodiment of the invention, the subject is a NYHA, class I subject.

Determining the amount of a natriuretic peptide or a cardiac troponin according to the present invention relates to measuring the amount or concentration, preferably semi-quantitatively or quantitatively. Measuring can be done directly or indirectly. Direct measuring relates to measuring the amount or concentration of the natriuretic peptide or cardiac troponin based on a signal which is obtained from the natriuretic peptide or cardiac troponin itself and the intensity of which directly correlates with the number of molecules of the peptide present in the sample. Such a signal—sometimes referred to herein as intensity signal—may be obtained, e.g., by measuring an intensity value of a specific physical or chemical property of the natriuretic peptide or cardiac troponin. Indirect measuring includes measuring of a signal obtained from a secondary component (i.e. a component not being the natriuretic peptide itself) or a biological read out system, e.g., measurable cellular responses, ligands, labels, or enzymatic reaction products.

In accordance with the present invention, determining the amount of the natriuretic peptide or cardiac troponin can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the natriuretic peptide or cardiac troponin. Moreover, the signal strength can, preferably, be correlated directly or indirectly (e.g. reverse-proportional) to the amount of polypeptide present in a sample. Further suitable methods comprise measuring a physical or chemical property specific for the natriuretic peptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on ELECSYS analyzers, Roche Diagnostics GmbH), CBA (an enzymatic cobalt binding assay, available for example on Roche/Hitachi analyzers), and latex agglutination assays (available for example on Roche/Hitachi analyzers). The methods and means for measurement also include point-of-care devices, such as the CARDIAC READER (available from Roche Diagnostics).

Point-of-care devices are generally understood as devices which enable measuring at the patient bedside. An example is the CARDIAC READER (available from Roche Diagnostics), in combination e.g. with test strips for NT-proBNP (available as "Cardiac proBNP" from Roche Diagnostics). Such test may employ two (preferably monoclonal) antibodies directed against the peptide of interest (e.g. a BNP-type peptide). The antibodies can be identical to the antibodies used e.g. in the ELECSYS or COBAS assays. E.g. the first antibody is labeled with biotin while the second antibody is labeled with gold particles. The test can be started by adding a small amount (e.g 150 μl) of blood sample onto the test strip (e.g. into a sample well of the test strip). The erythrocytes in the sample may be separated from the remaining plasma before or after addition to the test strip, e.g. if the sample flows through a suitable fleece (e.g. a glass fiber fleece). Said separating means (e.g. fleece) is preferably part of the test strip. The antibodies (preferably already present on the test strip) are dissolved in the remaining plasma. The antibodies are capable of binding to the peptide or polypeptide of interest, forming a three-membered sandwich complex. The antibodies (bound or unbound) flow through the strip into a detection zone. The detection zone comprises means for detecting the bound complex, e.g. it may comprise streptavidin. This immobilizes the complexes and visualizes the immobilized complex as a purple line by the gold-labeled antibody. Preferably, remaining free gold-labeled antibody may then move further down the strip where it is captured in a zone comprising a synthetic peptide or polypeptide comprising the epitope of the BNP-type peptide to be detected, visualized as a separate purple line. The presence of such second line can serve as a control because it indicates that the sample flow as worked correctly and the antibody is intact. the test strip may comprise a label indicating which peptide or polypeptide of interest can be detected with the strip. It may also comprise a barcode or other code readable by a device for optical measurement of the amount of label detectable in the detection zone. Such barcode may include information indicating which peptide or polypeptide of interest can be detected with the strip. The barcode may also include lot-specific information about the test strip.

The tests which lend themselves for a use in the present invention have a high sensitivity for the detection of a cardiac troponin, in particular troponin T and/or troponin I. The respective tests allow to measure troponin T in a concentration of down to about 0.001 ng/ml, or even less. A concentration of about 0.01 ng/ml can be determined with a reproducibility of 99% or more. Corresponding values apply for other cardiac troponins like troponin I, and these values are known to the person skilled in the art or are deducible from the values published in the literature.

The high sensitivity tests are based on essentially the same reagents and ingredients as the previous assay generation. Sensitivity has been increased by changing the geometry and/or the incubation time.

The CARDIAC READER itself comprises a camera (e.g. charge-coupled device, CCD) that optically records the detection zone of the test strip. Signal and control lines may be identified by a pattern recognition algorithm. The intensity of the label in the signal line is typically proportional to the amount of peptide or polypeptide of interest. The optical signal may be converted into a concentration via a lot-specific calibration curve which may be stored in a code chip. The agreement of calibration code and test lot may be checked by a barcode on the test strip.

In a preferred embodiment, the method for determining the amount of a natriuretic peptide or cardiac troponin comprises the steps of contacting a cell capable of eliciting a cellular response the intensity of which is indicative of the amount of the peptide with the peptide for an adequate period of time, and measuring the cellular response.

For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide.

In another preferred embodiment, the method for determining the amount of a natriuretic peptide or cardiac troponin comprises the step of measuring a specific intensity signal obtainable from the natriuretic peptide or cardiac troponin in the sample.

As described above, such a signal may be the signal intensity observed at an m/z variable specific for the natriuretic peptide or cardiac troponin observed in mass spectra or a NMR spectrum specific for the natriuretic peptide or cardiac troponin.

In another preferred embodiment, the method for determining the amount of a natriuretic peptide comprises the steps of contacting the peptide with a specific ligand, (optionally) removing non-bound ligand, measuring the amount of bound ligand.

The bound ligand will generate an intensity signal. Binding according to the present invention includes both covalent and non-covalent binding. A ligand according to the present invention can be any compound, e.g., a peptide, polypeptide, nucleic acid, or small molecule, binding to the natriuretic peptide or cardiac troponins described herein. Preferred ligands include antibodies, nucleic acids, peptides or polypeptides such as receptors for the natriuretic peptides or binding partners for the cardiac troponins and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the natriuretic peptide. Specific binding according to the present invention means that the ligand or agent should not bind substantially to ("cross-react" with) another peptide, polypeptide or substance present in the sample to be analyzed. Preferably, the specifically bound natriuretic peptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the ligand/natriuretic peptide or ligand/cardiac troponin complex or the ligand which was bound by the natriuretic peptide or cardiac troponin, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molcular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g. a light-sensitive film or a phosphor imager. Suitable measurement methods according the present invention also include precipitation (particularly immunoprecipitation), electro-chemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

In another preferred embodiment, the method for determining the amount of a cardiac troponin or a natriuretic peptide comprises contacting a solid support comprising a ligand for the natriuretic peptide or cardiac troponin as specified above with a sample comprising the natriuretic peptide or cardiac troponin and measuring the amount of natriuretic peptide or cardiac troponin which is bound to the support.

The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labelled, carrying different ligands. Methods of producing such arrays, for example based on solid-phase chemistry and photo-labile protective groups, are generally known (U.S. Pat. No. 5,744, 305).

The term "amount" as used herein encompasses the absolute amount of the natriuretic peptides or cardiac troponins, the relative amount or concentration of the natriuretic peptides or cardiac troponins as well as any value or parameter which correlates thereto. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., expression levels determined from biological read out systems in response to the peptides or intensity signals obtained from specifically bound ligands. It is to be understood that values correlating to the aforementioned amounts or parameters can also be obtained by all standard mathematical operations.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac troponin refers to troponin T and/or troponin I.

In the context of the present invention, troponin T is generally preferred over troponin I. However, the person skilled in the art is aware that in many or most cases the information obtained from measuring the amount of troponin I is as valuable as the information obtained from measuring troponin I, with both peptides emanating from cardiac muscle cells, i.e. the myocardium, and being released in case of the same events (a damage to the cell).

Accordingly, both troponins may be determined in the method of the present invention together, i.e. simultaneously or sequentially, or individually, i.e. without determining the other isoform at all.

Amino acid sequences for human troponin T and human troponin I are disclosed in Anderson, loc cit and Ferrieres 1998, Clinical Chemistry, 44: 487-493. The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the said cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation.

The term "natriuretic peptide" comprises atrial natriuretic peptide (ANP)-type and brain natriuretic peptide (BNP)-type peptides and variants thereof having the same predictive potential. Natriuretic peptides according to the present invention comprise ANP-type and BNP-type peptides and variants thereof (see e.g. Bonow, R. O. (1996). New insights into the cardiac natriuretic peptides. Circulation 93: 1946-1950). ANP-type peptides comprise pre-proANP, proANP, NT-proANP, and ANP. BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NTproBNP is 120 min longer than that of BNP, which is 20 min (Smith M W, Espiner E A, Yandle T G, Charles C J, Richards A M. Delayed metabolism of human brain natriuretic peptide reflects resistance to neutral endopeptidase. J Endocrinol. 2000; 167: 239-46.).

Preanalytics are more robust with NT-proBNP allowing easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller T, Gegenhuber A, et al., Clin Chem Lab Med 2004; 42: 942-4, supra; Wu A H, Packer M, Smith A, Bijou R, Fink D, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73.). Therefore, depending on the time-course or properties of interest, either measurement of the active or the inactive forms of the natriuretic peptide can be advantageous.

The most preferred natriuretic peptides according to the present invention are NT-proBNP or variants thereof. As briefly discussed above, the human NT-proBNP as referred to in accordance with the present invention is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, Bonow 1996, New Insights into the cardiac natriuretic peptides. Circulation 93: 1946-1950. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein.

The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999. Development of a novel, N-Terminal-proBNP (NT-proBNP) assay with a low detection limit. Scand J Clin Invest 59:177-181), Yeo et al. (Yeo 2003. Multicenter evaluation of the Roche NT-proBNP assay and comparison to the Biosite Triage assay. Clinica Chimica Acta 338:107-115), and in Example 1, below. Variants also include posttranslationally modified peptides such as glycosylated peptides.

A variant in accordance with the present invention is also a peptide or polypeptide which has been modified after collection of the sample, for example by covalent or non-covalent attachment of a label, particularly a radioactive or fluorescent label, to the peptide.

The term "sample" refers to a sample of a body fluid, to a sample of separated cells or to a sample from a tissue or an organ. Samples of body fluids can be obtained by well known techniques and include, preferably, samples of blood, plasma, serum, or urine. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein (i.e. the natriuretic peptides and the cardiac troponins).

Comparing as used herein encompasses comparing the amount of the natriuretic peptide or cardiac troponin comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired diagnosis in a suitable output format.

The term "reference amount" as used herein refers to an amount which allows assessing whether a subject suffers from an advanced ischemic heart disease, which is preferably symptomless, or another disease referred to in this specification by a comparison as referred to above. Accordingly, the reference may either be derived from a subject belonging to a risk group, as specified above, and/or a subject being healthy at least with respect to an advanced ischemic heart disease. The reference amount applicable for a subject may vary depending on various physiological parameters such as age, gender, or subpopulation. Thus, a suitable reference amount may be determined by the method of the present invention from a reference sample to be analyzed together, i.e. simultaneously or subsequently, with the test sample. In principle, it has been found in accordance with the present invention that during progression of ischemic heart disease the amount of cardiac troponins to be found, e.g., in plasma will also increase. Moreover, the more severe the ischemic heart disease will become, the higher the amount of natriuretic peptides in the plasma will be.

Thus, with respect to a healthy subject elevated plasma cardiac troponin and natriuretic peptide amounts shall be associated with a higher probability of suffering from an acute cardiovascular event or more severe forms of chronic heart failure. More preferably, it has been found in accordance with the present invention that a reference amount for the cardiac troponin of at least 0.003 ng/ml, preferably 0.1 ng/ml, in particular 0.5 ng/ml is indicative for an advanced ischemic coronary heart disease. Moreover, a reference amount of the cardiac troponin as cited beforehand in connection with a reference amount for the natriuretic peptide of at least 150 pg/ml, preferably 350 pg/ml, in particular 500 pg/ml is also indicative for (i.e. associated with a higher probability for developing) an advanced ischemic coronary heart disease.

The definitions and explanations of the terms made above and below apply accordingly for all embodiments described in this specification and the accompanying claims.

It follows from the above that in a preferred embodiment of the method of the present invention, a reference amount for the cardiac troponin of at least 0.003 ng/ml, optionally in combination with any cited reference amount of the natriuretic peptide is indicative of an advanced ischemic coronary heart disease.

In a preferred embodiment, the present invention permits to differentiate between a single vessel coronary heart disease and a multi-vessel coronary heart disease.

In the context of the present invention, the term "multi vessel coronary heart disease" designates a vessel occlusion which is more severe than a "single vessel coronary heart disease".

The term "differentiating" as used herein means to distinguish between a subject which suffers from a single vessel coronary heart disease and a subject suffering from a multi vessel heart disease.

The term "chronic heart failure" as used herein refers to chronic, i.e. permanent, heart failure. Heart failure is characterised by an impaired diastolic or systolic blood flow rate and, thus, by an impaired function of the heart. However, rather than exhibiting sudden ischemia accompanied by severe necrosis of the heart muscle cells, chronic heart failure as referred to herein is, preferably, accompanied by continuous necrotic events in heart muscle cells which result in a continuously developing impaired function of the heart.

Advantageously, the present invention—by providing the aforementioned method for differentially diagnosing an acute cardiovascular event and a chronic heart failure—allows to reliably and time—as well as cost-effectively distinguish between said disease conditions. Therefore, subjects suffering from the said diseases can be readily treated by specific and effective therapies rather than unspecific and ineffective therapies.

A subject which has been found to have an elevated troponin T level but has no symptoms will be subjected to a more intense diagnosis, in particular a catheter angiography, a virtual angiography using a contrast medium in connection with a computer tomogram in order to identify constrictions which may be opened, as the case may be, by balloon dilatation or a stent. By this, MI may be avoided, and the cardiac function can be maintained.

A subjected which has been found to have an elevated troponin T level but has no symptoms may also be subjected to a treatment lowering the pressure on the interior walls of the myocardium and hence lowering the probability for the occurrence of a necrosis.

Specifically preferred embodiments of the method of the present invention are referred to as follows:

In a preferred embodiment of the method of the present invention, a reference amount for the cardiac troponin of at least 0.003 ng/ml and a reference amount for the natriuretic peptide of at least 150 pg/ml are indicative for a serious advanced coronary artery disease. In a more preferred embodiment, the reference amount for the cardiac troponin is at least 0.1 ng/ml and the reference amount for the natriuretic peptide is at least 350 pg/ml. In a particularly preferred embodiment, the reference amount for the cardiac troponin is at least 0.5 ng/ml and the reference amount for the natriuretic peptide is at least 500 pg/ml.

In a preferred embodiment of the method of the present invention, the natriuretic peptide is BNP, more preferably, NT-proBNP.

In a further preferred embodiment of the method of the present invention, the natriuretic peptide is ANP, more preferably, NT-proANP.

In a furthermore preferred embodiment of the method of the present invention, said cardiac troponin is troponin T and/or troponin I.

Also, in a preferred embodiment of the method of the present invention, said subject is a human.

The present invention further relates to a device for diagnosing an advanced ischemic coronary heart disease comprising means for determining the amount of a cardiac troponin in a sample of a subject and optionally means for determining the amount of a natriuretic peptide in a sample.

The term "device" as used herein relates to a system of means comprising at least the aforementioned means operatively linked to each other as to allow the prediction. Preferred means for determining the amount of the natriuretic peptides or cardiac troponins and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to diagnose an acute cardiovascular event or other disease referred to herein. Preferably, the means are comprised by a single device in such a case. Said device may include an analyzing unit for the measurement of the amount of the peptides in a sample and a computer unit for processing the resulting data for the differential diagnosis. Alternatively, where means such as test strips are used for determining the amount of the peptides, the means for diagnosing may comprise control strips or tables allocating the determined amount to an amount known to be accompanied with an acute cardiovascular event or other diseases referred to herein or an amount known to be indicative for a healthy subject. The test strips are, preferably, coupled to a ligand which specifically binds to the natriuretic peptide or cardiac troponin. The strip or device, preferably, comprises means for detection of the binding of said peptides to the said ligand. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of diagnostic raw data which need interpretation by the clinician. Preferably, the output of the device are, however, processed diagnostic raw data the interpretation of which does not require a clinician, i.e. it should be inevitably clear from the output whether the subject suffers from mild or moderate heart failure. Further preferred devices comprise the analyzing units/devices (e.g., biosensors, arrays, solid supports coupled to ligands specifically recognizing the natriuretic peptide, Plasmon surface resonace devices, NMR spectrometers, mass-spectrometers etc.) or evaluation units/devices referred to above in accordance with the method of the invention.

Moreover, encompassed by the present invention is also the use of a device comprising means for determining the amount of a cardiac troponin in a sample of a subject and optionally, means for determining the amount of a natriuretic peptide in a sample for diagnosing an advanced ischemic coronary heart disease, which preferably is symptomless, in a subject.

Finally, the present invention relates to a kit for carrying out the method of the present invention comprising means for determining the amount of a cardiac troponin in a sample of a subject and optionally, means for determining the amount of a natriuretic peptide in a sample.

The term "kit" as used herein refers to a collection of the aforementioned means, preferably, provided in separately or within a single container. The container, also preferably, comprises instructions for carrying out the method of the present invention.

Optionally, the kit may additionally comprise a user's manual for interpreting the results of any measurement(s) with respect to diagnosing an advanced coronary artery disease and/or its complications. Particularly, such manual may include information about what measured level corresponds to what grade of risk. This is outlined in detail elsewhere in this specification. Additionally, such user's manual may provide instructions about correctly using the components of the kit for measuring the level(s) of the respective biomarker.

All references cited in this specification are herewith incorporated by reference with respect to their entire disclosure content and the disclosure content specifically mentioned in this specification.

The following Example shall merely illustrate the invention. It shall not be construed, whatsoever, to limit the scope of the invention.

Specific Embodiments

EXAMPLE 1

A total of 235 asymptomatic individuals at suspected risk of arteriosclerosis received an EGC, an echocardiography as well as a coronary angiogram.

According to the results of the echocardiography a systolic dysfunction was diagnosed if the LVEF was below 40%. Patients with a LVEF above 60% were considered to have no systolic dysfunction, patients with a LVEF between 40-60% were considered indeterminate with respect to systolic dysfunction. In addition left atrium size is well as septum thickness were measured.

Coronary artery disease was classified in one, two and three vessel disease. Vessel disease was assumed if there was one or more vessel stenosis which narrowed the vessel volume at least 50%.

In addition to these examinations medical history was taken with regard to risk behavior which includes smoking, diabetes, arterial hypertension, previous myocardial infarction as well as lipid abnormalities, specifically cholesterol levels, LDL levels and triglycerides levels.

Sensitive troponin T was tested by a newly developed sensitive troponin T assay (Roche Diagnostics, Mannheim, Germany), NT-proBNP was also measured by immunoassay (Roche Diagnostics, Mannheim, Germany), CD40 ligand was tested in plasma samples using an immunoassay from Roche Diagnostics, Mannheim, Germany, and NT-proANP was tested by microtiter plate immunoassay manufactured by Biomedica, Wien, Austria. All tests were performed according to the instructions of the manufacturer. The results are given below in Table 1.

TABLE 1

High-sensitive TnT quartile in patients with documented coronary artery disease.

| | Hs-TnT [ng/ml] N = 235 Diagnose Group I | | | |
|---|---|---|---|---|
| | 1st Quartile | 2nd Quartile | 3rd Quartile | 4th Quartile |
| N | 49 | 59 | 58 | 69 |
| Median Hs-TnT ng/ml | 0 | 0.00292 | 0.00954 | 0.05022 |
| range | 0-0.00069 | 0.0008-0.00541 | 0.00555-0.0176 | 0.0183-0.7079 |
| Age, median | 64 | 67 | 67 | 69 |
| Male (n) | 22 | 37 | 31 | 51 |
| Female (n) | 27 | 22 | 17 | 18 |
| Height (m) median | 1.69 | 1.70 | 1.69 | 1.70 |
| Weight (kg) | 75.5 | 77.0 | 82.0 | 82.0 |
| LVEF (%) | | | | |
| >60% | 42 | 51 | 38 | 21 |
| 40-60% | 2 | 3 | 3 | 15 |
| <40% | 5 | 5 | 17 | 33 |
| | | | $p < 0.0001^{***}$ | |
| LA (mm), median | 39.0 | 40.0 | 41.0 | 40.0 |
| SEP (mm), median | 12.0 | 12.0 | 13.0 | 12.0 |

TABLE 1-continued

High-sensitive TnT quartile in patients with documented coronary artery disease.

Hs-TnT [ng/ml] N = 235
Diagnose Group I

|  | 1st Quartile | 2nd Quartile | 3rd Quartile | 4th Quartile |
|---|---|---|---|---|
| Coronary artery disease |  |  |  |  |
| 1-vessel disease | 8 | 11 | 7 | 14 |
| 2-vessel disease | 15 | 12 | 12 | 11 |
| 3-vessel disease | 9 | 14 | 26 | 27 |
|  |  | $p = 0.0290*$ |  |  |
| Smoker (n) | 16 | 32 | 28 | 39 |
|  |  | $p > 0.05$ (n.s.) |  |  |
| Diabetes (n) | 9 | 10 | 23 | 25 |
| Art. Hypertension (n) | 34 | 43 | 44 | 43 |
| Heart Rate | 67 | 62 | 70 | 73 |
| Previous MI (n) | 9 | 14 | 24 | 38 |
| ECG (n) | 47 | 53 | 54 | 61 |
| Median Cholesterol mg/dl | 233.0 | 229.0 | 224.0 | 214.0 |
| Median LDL mg/dl | 149.9 | 138.6 | 145.6 | 133.0 |
| Median Triglycerides mg/dl | 143.5 | 156.0 | 169.0 | 151.0 |
|  |  | $p < 0.0001$ |  |  |
| Median NT-proBNP pg/ml | 116.8 | 175.6 | 359.7 | 1046.0 |
| range | 5.0-5942 | 11.2-12703 | 5.0-14953 | 16.3-21116 |
|  |  | $p < 0.0001$ |  |  |
| Median NT-proANP pg/ml | 2016.0 | 2555.9 | 3485.0 | 5364.2 |
| range | 540-11640 | 901-9536 | 1189-11955 | 1185-27978 |
|  |  | $p > 0.05$ (n.s.) |  |  |
| Median sCD40L ng/ml | 1.155 | 1.023 | 1.104 | 1.550 |
| range | 0.212-5.818 | 0.184-3.621 | 0.009-7.454 | 0.080-5.482 |

EXAMPLE 2

Hypothetically, a 57 year old man with a history of type 2 diabetes has repeatedly chest pain for a short period of time mostly unrelated to exercise. He undergoes coronary angiography for further clarification which is without pathological changes. Troponin T is <0.01, NT-proBNP is 92 pg/ml.

EXAMPLE 3

Hypothetically, a 42 year old man with a family history of myocardial infarction and in good physical health agrees to a medical check up. A reduced LVEF of 25% is found in the echocardiography, the coronary angiography reveals a three vessel disease with two stenoses ≧90% which is treated by stent implantation. Troponin T is 0.04 and NT-proBNP is 920 pg/ml.

EXAMPLE 4

A total of 26 patients with advanced cardiovascular disease and detectable sensitive troponin T were followed for a total of 12 months. After the 12 months observation period all patients remained troponin T positive and had no symptoms prior to examination. Median TnT levels were initially <0.009 ng/ml and remained 0.009 ng/ml after 12 months. Data indicate that troponin T positivity remains a stable finding and proper association to defined risk groups independent from time point of blood collection, thereby showing that the level of troponin may remain elevated over months in case of asymptomatic patients.

What is claimed is:

1. A method for diagnosing ischemic coronary artery disease caused by a coronary vessel disease in an asymptomatic patient belonging to a risk group selected from the group consisting of smokers, patients suffering from diabetes, obese patients, patients suffering from hyperlipidemia, patients suffering from arterial hypertension, patients having a family history of any of coronary artery disease, myocardial infarction, or stroke, and patients suffering from rheumatoid arthritis, the method comprising the steps of:
   measuring in vitro an amount of a cardiac troponin in a sample from the patient,
   measuring in vitro an amount of a natriuretic peptide in the sample,
   comparing the amount of the cardiac troponin measured with a reference amount of the cardiac troponin and comparing the amount of natriuretic peptide measured with a reference amount of natriuretic peptide, wherein the reference amounts are derived from asymptomatic individuals, and
   diagnosing the disease where the measured amounts are elevated over the reference amounts, wherein the reference amount of the cardiac troponin is at least 0.003 ng/ml and the reference amount of natriuretic peptide is at least 150 pg/ml.

2. The method according to claim 1 wherein the reference amount of the cardiac troponin is between about 0.003 ng/ml and 0.1 mg/ml.

* * * * *

UNITED STATES PATENT AND TRADEMARK OFFICE
CERTIFICATE OF CORRECTION

PATENT NO. : 7,927,812 B2  Page 1 of 1
APPLICATION NO. : 11/837714
DATED : April 19, 2011
INVENTOR(S) : Georg Hess and Andrea Horsch It is certified that error appears in the above-identified patent and that said Letters Patent is hereby corrected as shown below:

Title page, item (75) "Inventors" replace "Andrea Hess" with --Andrea Horsch--.

Signed and Sealed this
Twenty-first Day of June, 2011

David J. Kappos
*Director of the United States Patent and Trademark Office*